US012682494B2

(12) United States Patent
Namgung et al.

(10) Patent No.: US 12,682,494 B2
(45) Date of Patent: Jul. 14, 2026

(54) METHOD FOR CALIBRATING INTRAORAL SCANNER

(71) Applicant: Huvitz Co., Ltd., Anyang-si (KR)

(72) Inventors: Myoung Namgung, Anyang-si (KR); Min Soo Cho, Anyang-si (KR); Weon Joon Lee, Anyang-si (KR)

(73) Assignee: Huvitz Co., Ltd., Anyang-si (KR)

( * ) Notice: Subject to any disclaimer, the term of this patent is extended or adjusted under 35 U.S.C. 154(b) by 132 days.

(21) Appl. No.: 18/619,866

(22) Filed: Mar. 28, 2024

(65) Prior Publication Data

US 2024/0346693 A1     Oct. 17, 2024

(30) Foreign Application Priority Data

Apr. 11, 2023     (KR) ........................ 10-2023-0047440

(51) Int. Cl.
 *G06T 7/80* (2017.01)
 *A61B 5/00* (2006.01)
 (Continued)

(52) U.S. Cl.
 CPC .............. *G06T 7/80* (2017.01); *A61B 5/0088* (2013.01); *G06T 7/0012* (2013.01); *G06T 7/50* (2017.01);
 (Continued)

(58) Field of Classification Search
 CPC .......... G06T 7/80; G06T 7/0012; G06T 7/50; G06T 2207/30036; G06T 7/521;
 (Continued)

(56) References Cited

U.S. PATENT DOCUMENTS

| 10,977,829 B2 * | 4/2021 | Ma | ............................ G06T 7/55 |
| 11,096,765 B2 * | 8/2021 | Atiya | ..................... A61C 9/006 |

(Continued)

FOREIGN PATENT DOCUMENTS

| CN | 101245994 A | 8/2008 |
| KR | 10-2018-0110355 A | 10/2018 |
| KR | 10-2152921 B1 | 9/2020 |

OTHER PUBLICATIONS

European search report for European counterpart application No. 24165221.3 dated Sep. 17, 2024.

(Continued)

*Primary Examiner* — John R Schnurr
(74) *Attorney, Agent, or Firm* — UNITED ONE LAW GROUP LLC; Kongsik Kim; Jhongwoo Peck

(57) ABSTRACT

A method of calibrating an intraoral scanner includes irradiating light of a third color using a projector onto a first calibration plate having a background of a first color and patterns of a second color, which are arranged at predetermined intervals within the background; obtaining an image of the patterns with an increased contrast by photographing the first calibration plate with a camera; calibrating the camera by comparing the image of the patterns with actual positions of the patterns; irradiating the first calibration plate with a patterned light having a predetermined pattern of a fourth color using the projector; obtaining an image of a pattern formed by the patterned light of the projector by photographing the first calibration plate with the camera; and calibrating the projector by comparing the pattern image with a target irradiation position of a pattern irradiated by the projector.

2 Claims, 6 Drawing Sheets

(51) Int. Cl.

| | | |
|---|---|---|
| *G06T 7/00* | (2017.01) | |
| *G06T 7/50* | (2017.01) | |
| *G06V 10/141* | (2022.01) | |
| *G06V 10/56* | (2022.01) | |

(52) U.S. Cl.
CPC ........... *G06V 10/141* (2022.01); *G06V 10/56* (2022.01); *G06T 2207/30036* (2013.01)

(58) Field of Classification Search
CPC ..... A61B 5/0088; A61B 1/00057; A61B 1/24; A61B 1/00194; A61B 1/0605; A61B 5/0062; A61B 2560/0223; G06V 10/141; G06V 10/56; H04N 17/002; H04N 23/56; H04N 9/3194; H04N 9/3185; A61C 9/006; A61C 9/0053; A61C 19/04; G01B 11/25

See application file for complete search history.

(56) References Cited

U.S. PATENT DOCUMENTS

| | | | | | |
|---|---|---|---|---|---|
| 11,650,045 | B2 * | 5/2023 | Kjaer | ..................... | G02B 30/60 |
| | | | | | 348/46 |
| 12,263,064 | B2 * | 4/2025 | Elbaz | ................... | A61B 5/1079 |
| 12,274,600 | B2 * | 4/2025 | Saphier | .................. | A61C 9/006 |
| 2008/0285843 | A1 * | 11/2008 | Lim | ..................... | G06V 10/145 |
| | | | | | 382/154 |
| 2010/0245684 | A1 * | 9/2010 | Xiao | .................... | H04N 9/3194 |
| | | | | | 348/745 |
| 2014/0022283 | A1 * | 1/2014 | Chan | .................... | H04N 9/3185 |
| | | | | | 345/633 |
| 2014/0078260 | A1 * | 3/2014 | Taubin | ................. | H04N 13/246 |
| | | | | | 348/46 |
| 2015/0124055 | A1 * | 5/2015 | Kotake | .............. | G01B 11/2513 |
| | | | | | 348/46 |
| 2015/0189267 | A1 * | 7/2015 | Kaji | .......................... | G06T 3/18 |
| | | | | | 348/187 |
| 2015/0268035 | A1 * | 9/2015 | Furihata | ............... | G01B 11/002 |
| | | | | | 348/136 |
| 2016/0180511 | A1 * | 6/2016 | Zhou | .................... | H04N 9/3185 |
| | | | | | 348/187 |
| 2017/0032530 | A1 * | 2/2017 | Furihata | ............... | G01B 11/254 |
| 2017/0161943 | A1 * | 6/2017 | Lam | .......................... | G06T 7/20 |
| 2019/0000412 | A1 * | 1/2019 | Wong | ..................... | A61B 6/584 |
| 2019/0388193 | A1 * | 12/2019 | Saphier | ................... | G06T 17/00 |
| 2019/0388194 | A1 * | 12/2019 | Atiya | ................. | A61B 1/00193 |
| 2020/0404243 | A1 * | 12/2020 | Saphier | .................. | A61C 9/006 |
| 2022/0357151 | A1 * | 11/2022 | Liang | ................. | G01B 11/2504 |
| 2024/0197448 | A1 * | 6/2024 | Saphier | .................. | A61C 9/006 |
| 2024/0212210 | A1 * | 6/2024 | Gao | ........................ | B25J 9/1697 |
| 2024/0291952 | A1 * | 8/2024 | Lepoittevin | .......... | G06V 10/225 |
| 2024/0358482 | A1 * | 10/2024 | Dafna | ................. | A61B 1/0605 |
| 2025/0341392 | A1 * | 11/2025 | Wang | ................. | G01B 11/2504 |

OTHER PUBLICATIONS

Zhang, "Pixel-wise structured light calibration method with a color calibration target," Optics Express, vol. 30, No. 20, Sep. 26, 2022, pp. 35817-35827.

Huang et al., "A Single-shot-per-pose Camera-Projector Calibration System For Imperfect Planar Targets," 2018 IEEE International Symposium on Mixed and Augmented Reality Adjunct (Ismar-Adjunct), IEEE, Oct. 16, 2018, pp. 15-20.

* cited by examiner (a)                    (b)

100

110

120

METHOD FOR CALIBRATING INTRAORAL SCANNER

CROSS-REFERENCE TO RELATED APPLICATION

This application claims priority from Korean Application No. 10-2023-0047440 filed Apr. 11, 2023, which is incorporated herein by reference in its entirety.

TECHNICAL FIELD

The present disclosure relates to a method for calibrating an intraoral scanner, and more particularly, to a method for calibrating an intraoral scanner that can calibrate a camera and a projector used in the intraoral scanner.

RELATED ART

An intraoral scanner is a type of three-dimensional scanner that obtains multiple optical images of a target object through a series of scanning sequences and generates three-dimensional model data for the target object by combining them.

An intraoral scanner refers to a device configured to be suitable for obtaining a series of optical images of parts of the human body, in particular, structures inside the oral cavity such as teeth and gums out of these three-dimensional scanners.

FIG. 6 is a diagram showing the principle of photographing the shape of an oral structure in a typical intraoral scanner. As shown in FIG. 6, the typical intraoral scanner includes a projector 12 including a light source that irradiates a measurement light to an oral structure S such as a tooth, and a camera 14 including an image sensor that detects light reflected from the oral structure S and obtains the surface shape of the oral structure S. The measurement light (e.g., visible light) emitted from the light source of the projector 12 is irradiated onto the oral structure S inside the oral cavity, and the light reflected from the oral structure S is detected by the image sensor of the camera 14, thereby obtaining the surface shape information of the oral structure S. At this time, the two-dimensional image of the oral structure S detected by the camera 14 is converted into a three-dimensional image using triangulation or the like, and multiple three-dimensional partial images can be combined to obtain a whole three-dimensional image of the oral structure S. A digital light processing (DLP) projector may be used as the projector 12.

In the processes of manufacturing or using the intraoral scanner, errors may occur in the three-dimensional model data, i.e., the three-dimensional image obtained by the intraoral scanner. For example, if a part of the intraoral scanner, for example, a scanner tip having an optical element such as a reflector, is replaced for hygiene purposes, an error may occur in the three-dimensional model data obtained by the intraoral scanner. Therefore, in order to obtain accurate three-dimensional model data, error correction work, i.e., calibration, on the intraoral scanner must be performed frequently.

FIG. 1 is a diagram showing one example of conventional pattern plates used, respectively, for calibration of a camera 14 and a projector 12 of an intraoral scanner. As shown in FIG. 1, conventionally, a camera calibration plate 50 (see (a) in FIG. 1) for correcting the camera 14 and a projector calibration plate 60 (see (b) in FIG. 1) for correcting the projector 12 are used, respectively. In the camera calibration plate 50, a black dot pattern 52 is formed on a white background color. The projector calibration plate 60 is a plate colored with a non-reflective matte white paint.

In a conventional method of correcting the camera 14 of the intraoral scanner, image data of the camera calibration plate 50 is obtained by photographing the camera calibration plate 50 with the camera 14, and the position, settings, and the like of the camera 14 can be corrected by analyzing the shape, position, and the like of the dot pattern 52.

In a conventional method of correcting the projector 12 of the intraoral scanner, a measurement light having a predetermined pattern is emitted (irradiated) onto the projector calibration plate 60 via the projector 12, image data is obtained by photographing the pattern of the measurement light formed on the calibration plate 60 with the camera 14, then the obtained image data is analyzed, the state in which the measurement light pattern of the projector 12 is irradiated onto the calibration plate 60 is analyzed, and the position, settings, and the like of the projector 12 can be corrected. For example, when a measurement light pattern with a line width of 1 mm is emitted (irradiated), it is analyzed whether a measurement light pattern with a line width of 1 mm is formed identically on the calibration plate 60, and the position, settings, and the like of the projector 12 can thus be corrected.

In these conventional calibration methods, different calibration plates 50 and 60 must be used to calibrate the camera 14 or the projector 12, respectively. In addition, since the calibration of the camera 14 or the projector 12 is performed separately, the calibration execution time and processing procedure become complicated. In other words, there is an inconvenience that the user has to perform each calibration while changing the calibration plates 50 and 60.

PRIOR ART LITERATURE

Patent Documents (Patent Document 1) Korean Patent Publication No. 10-2018-0110355

(Patent Document 2) Korean Patent No. 10-2152921

SUMMARY

It is an object of the present disclosure to provide a method for calibrating an intraoral scanner that performs calibration of both a camera and a projector by using a single calibration plate.

It is another object of the present disclosure to provide a method for calibrating an intraoral scanner that can perform calibration of a camera and a projector in a simplified procedure within a short time.

In order to achieve the above objects, the present disclosure provides a method of calibrating an intraoral scanner comprising the steps of: irradiating an illumination light of a third color by using a projector 12 onto a first calibration plate 100 having a background 110 of a first color and patterns 120 of a second color different from the first color, which are arranged at predetermined intervals within the background 110; obtaining an image of the patterns 120 with an increased contrast by photographing the first calibration plate 130 with an increased contrast between the background 110 and the patterns 120 with a camera 14; calibrating the camera 14 by comparing the image of the patterns 120 obtained by photographing with the camera 14 with actual positions of the patterns 120 formed on the calibration plate 100; irradiating the first calibration plate 100 with a patterned light having a predetermined pattern of a fourth color by using the projector 12; obtaining an image of a pattern 152 formed by the patterned light of the projector 12 by photographing a first calibration plate 150 with the pattern 152 of the patterned light formed thereon with the camera 14; and calibrating the projector 12 by comparing the pattern image 152 of the patterned light obtained by photographing with the camera 14 with a target irradiation position of a pattern irradiated by the projector 12, wherein the first color and the second color are set such that a contrast between the background 110 and the patterns 120 increases when the first calibration plate 100 is illuminated with the illumination light of the third color, and the predetermined pattern of the fourth color irradiated by the patterned light is set so as to cover the patterns 120 formed on the first calibration plate 100 and so that the contrast between the background 110 and the patterns 120 formed on the first calibration plate 100 is reduced.

In addition, the present disclosure provides a method of calibrating an intraoral scanner comprising the steps of: obtaining an image of patterns 320 by photographing a second calibration plate 300 having a background 310 and the patterns 320 arranged at predetermined intervals within the background 310 with a camera 14; calibrating the camera 14 by comparing the image of the patterns 320 obtained by photographing with the camera 14 with actual positions of the patterns 320 formed on the calibration plate 300; causing a pattern 332 of a patterned light to be formed in an empty space between the patterns 320 formed on the second calibration plate 300 by irradiating the second calibration plate 300 with the patterned light having a predetermined pattern by using a projector 12; obtaining an image of the pattern 332 formed by the patterned light of the projector 12 by photographing the second calibration plate 330 with the pattern 332 of the patterned light formed thereon with the camera 14; and calibrating the projector 12 by comparing the pattern image 332 of the patterned light obtained by photographing with the camera 14 with a target irradiation position of a pattern irradiated by the projector 12.

The method for calibrating an intraoral scanner in accordance with the present disclosure can perform calibration of both the camera and the projector by using a single calibration plate and can perform the calibration of the camera and the projector in a simplified procedure within a short time.

DETAILED DESCRIPTION

Hereinafter, the present disclosure will be described in detail with reference to the accompanying drawings.

Figure 6:
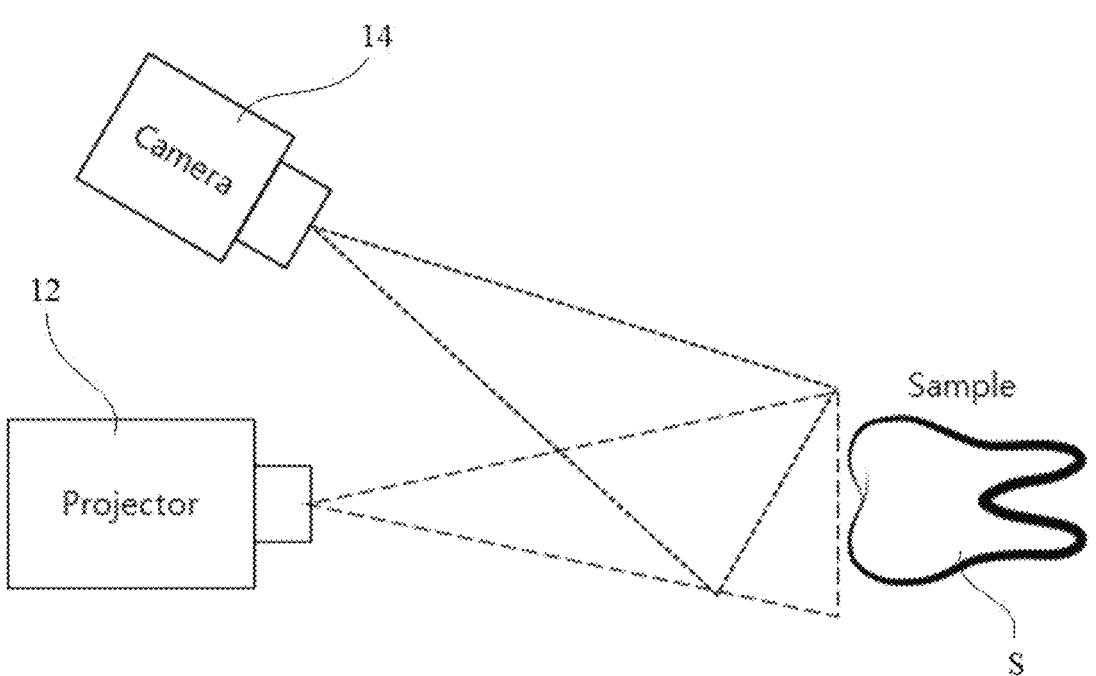
FIG. 6 is a diagram for describing the principle of photographing the shape of an oral cavity in a typical intraoral scanner.

As shown in FIG. 6, an intraoral scanner includes a projector 12 and a camera 14, and the projector 12 irradiates a measurement light onto an oral structure S such as a tooth and the camera 14 obtains a surface shape image of the oral structure S by detecting the measurement light reflected from the oral structure S. A method for calibrating an intraoral scanner in accordance with the present disclosure calibrates the projector 12 and the camera 14 of the intraoral scanner.

Figure 1:
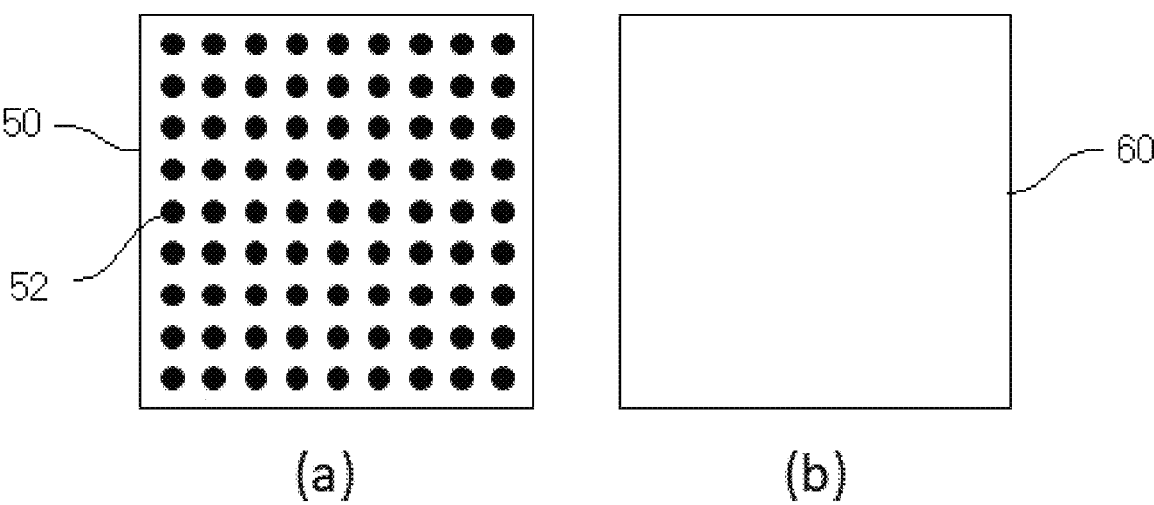
FIG. 1 is a diagram showing conventional pattern plates for calibrating a camera and a projector of an intraoral scanner, respectively.
Figure 2:
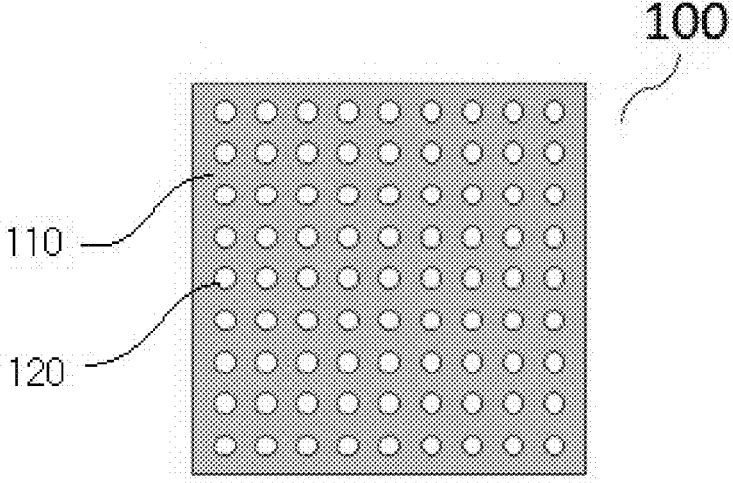
FIG. 2 is a diagram showing a first calibration plate 100 used in a method for calibrating an intraoral scanner in accordance with one embodiment of the present disclosure.

FIG. 2 is a diagram showing a first calibration plate 100 used in a method for calibrating an intraoral scanner in accordance with one embodiment of the present disclosure. The method for calibrating an intraoral scanner in accordance with one embodiment of the present disclosure calibrates both the camera 14 and the projector 12 of the intraoral scanner by using a single first calibration plate 100 as shown in FIG. 2. Here, 'calibrating both the camera 14 and the projector 16' does not necessarily mean that the calibrations are performed simultaneously in time but means calibrating both the camera 14 and the projector 12 by using a single first calibration plate 100. The first calibration plate 100 that can be used in the present disclosure is used to correct the camera 14 and is also used to correct the projector 12, and can thus be called a composite calibration plate.

The camera 14 and the projector 12 can be calibrated by irradiating the first calibration plate 100 with a measurement light (an illumination light or patterned light) via the projector 12 of the intraoral scanner and then analyzing the image of the first calibration plate 100 obtained by photographing the calibration plate 100 irradiated with the illumination light or patterned light with the camera 14.

The projector 12 may include a light source capable of irradiating (emitting) an illumination light or patterned light, and the illumination light or patterned light may have a color of blue (B), green (G), red (R), or a combination thereof. The projector 12 may emit (irradiate) the illumination light to the calibration plate 100 or emit (irradiate) the patterned light to the calibration plate 100, depending on the calibration of the camera 14 or the projector 12. Specifically, the projector 12 emits (irradiates) an illumination light of a particular color in order to calibrate the camera 14 of the intraoral scanner. The projector 12 emits (irradiates) a patterned light of a particular color and a particular pattern in order to calibrate the projector 14 of the intraoral scanner.

As shown in FIG. 2, the first calibration plate 100 is a plate having a background 110 of a first color, and patterns 120 of a second color different from the first color, which are arranged at predetermined intervals within the background 110. For example, the first calibration plate 100 may be a plate of various materials, for example, a square plate of glass material, and the background 110 and the patterns 120 may be formed on one side of the plate.

In the first calibration plate 100, by masking predetermined patterns, for example, dot patterns, on a white plate of glass material and then coating the plate 100 with a first color, the background 110 may be formed in the first color and the masked patterns 120 may be formed in the second color, for example, white.

The patterns 120 of the second color may be patterns arranged in a predetermined shape so as to allow the camera 14 to be calibrated, and are dot patterns arranged at predetermined intervals as shown in FIG. 2, for example. The diameter of the dots forming the dot patterns is, for example, about 0.25 mm, and the spacing (separation distance) between the dots is, for example, 0.1 to 0.4 mm, specifically 0.2 to 0.3 mm, and particularly specifically about 0.25 mm. The dot patterns formed on the first calibration plate 100 may vary depending on the size of the plate 100, but may be formed in the form of a 9×9 square matrix, as shown in FIG. 2, for example. Since the actual position and size of the patterns 120 are predetermined, an image of the patterns 120 is obtained by photographing the patterns 120 with the camera 14, and then the camera 14 may be calibrated, i.e., corrected so that the image of the patterns 120 obtained by photographing with the camera 14 corresponds to the actual position and size of the patterns 120.

Figure 3:
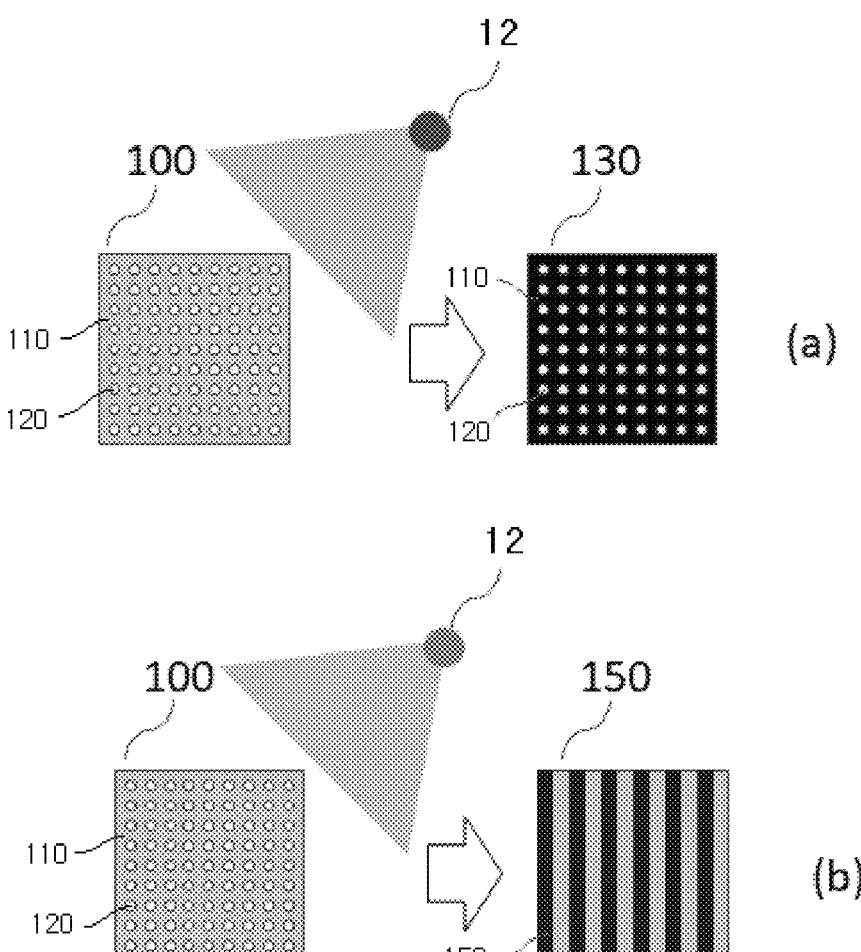
FIG. 3 is a diagram for describing a method of calibrating the camera and the projector of the intraoral scanner by using the first calibration plate, according to one embodiment of the present disclosure.

FIG. 3 is a diagram for describing a method of calibrating the intraoral scanner, specifically the camera 14 and the projector 12 of the intraoral scanner by using the first calibration plate 100, according to one embodiment of the present disclosure;

As shown in (a) of FIG. 3, in order to calibrate the camera 14 of the intraoral scanner according to the present disclosure, an illumination light of a third color is irradiated using the projector 12 onto the first calibration plate 100 having the background 110 of the first color and the patterns 120 of the second color different from the first color, which are arranged at predetermined intervals within the background 110.

The first color and the second color are set such that the contrast between the background 110 and the patterns 120 increases when the first calibration plate 100 is illuminated with the illumination light of the third color. For example, as shown in (a) of FIG. 3, if the first color of the background 110 is blue, the second color of the patterns 120 is white, and the third color of the illumination light is red, then the blue color of the first color is inverted to a darker color and the contrast between the color of the background 110 and the color of the patterns 120 is increased, thereby causing the patterns 120 to be observed more clearly when the first calibration plate 100 is entirely illuminated with the illumination light of the third color, i.e., red.

Next, the first calibration plate 130 with an increased contrast between the background 110 and the patterns 120 is photographed with the camera 14, thereby obtaining an image of the patterns 120 with the increased contrast.

Next, the camera 14 is calibrated by comparing the image of the patterns 120 obtained by photographing with the camera 14 with the actual position of the patterns 120 formed on the calibration plate 100. Such calibration of the camera 14 can be performed in a typical manner. Specifically, the camera 14 is calibrated such that the image of the patterns 120 obtained by photographing with the camera 14 corresponds to the actual position of the patterns 120 formed on the calibration plate 100. For example, the position, settings, and the like of the camera 14 are adjusted so that the image of the patterns 120 obtained by photographing with the camera 14 and the actual position of the patterns 120 formed on the calibration plate 100 are proportional to each other without distortion.

Preferably, in the calibration of the camera 14, the projector 12 emits the illumination light of the third color without a pattern so as to cover the entire area of the first calibration plate 100. The background 110 of the calibration plate 100 irradiated with the illumination light of the third color is inverted to, for example, a dark color by the color combination of the first color and the third color, and thus, the patterns 120 are observed more clearly. In other words, since the contrast between the color of the background 110 and the color of the patterns 120 of the calibration plate 100 is increased, a first calibration plate image 130 with improved discriminability of the patterns 120 is obtained.

As shown in (b) of FIG. 3, in order to calibrate the projector 12 of the intraoral scanner according to the present disclosure, a patterned light having a predetermined pattern of a fourth color is irradiated onto the first calibration plate 100 by using the projector 12.

The predetermined pattern of the fourth color irradiated by the patterned light is set so as to cover the patterns 120 formed on the first calibration plate 100 and so that the contrast between the patterns 120 and the background 110 formed on the first calibration plate 100 is reduced. Preferably, when the patterned light having the predetermined pattern of the fourth color is irradiated onto the first calibration plate 100, the predetermined pattern of the fourth color irradiated by the patterned light covers the patterns 120 of the second color formed on the first calibration plate 100, and thus the patterns 120 of the second color formed on the first calibration plate 100 are not visible or become weak and substantially only the pattern 152 of the patterned light appears on the first calibration plate 100. For example, as shown in (b) of FIG. 3, the first color of the background 110 of the first calibration plate 100 is blue, the second color of the patterns 120 is white, and the fourth color of the patterned light is blue, and the pattern 152 of the patterned light may be formed to cover the patterns 120 of the second color formed on the first calibration plate 100. For example, the pattern 152 of the patterned light may be in the form of a stripe covering the patterns 120 formed on the first calibration plate 100. In this case, when the first calibration plate 100 is illuminated with 'the patterned light having the predetermined pattern 152 of blue (fourth color)', the patterns 120 of the second color formed on the first calibration plate 100 are covered with the blue stripe pattern 152 of the patterned light and become invisible or weak. In other words, the contrast between the patterns 120 and the background 110 formed on the first calibration plate 100 decreases, and substantially only the blue stripe pattern 152 of the patterned light appears on the first calibration plate 100.

The colors (first color and second color) of the first calibration plate 100 and the fourth color of the patterned light may be set so that the contrast, i.e., the discriminability, of the patterns 120 formed on the first calibration plate 100 is weakened, and for example, the fourth color may be the same color as the first color. For example, the first color may be blue, and the fourth color may be blue with a lower brightness than the first color. In this case, the patterns 120 of the first calibration plate 100 are covered with the fourth color similar to the first color, and thus, the boundary between the background 110 and the patterns 120 gets vague (i.e., the contrast is reduced) and the patterns 120 become unidentifiable.

Next, the first calibration plate 150 with the pattern 152 of the patterned light formed thereon is photographed with the camera 14, and an image of the pattern 152 formed by the patterned light of the projector 12 is obtained.

Next, the projector 12 is calibrated by comparing the pattern image 152 of the patterned light obtained by photographing with the camera 14 with the target irradiation position of the pattern irradiated by the projector 12. Such calibration of the projector 12 can be performed in a typical manner. Specifically, the projector 12 is calibrated such that the position of the pattern image 152 of the patterned light obtained by photographing with the camera 14 corresponds to the target irradiation position of the pattern irradiated by the projector 12. For example, if the target irradiation position of the pattern irradiated by the projector 12 and the position of the image 152 of the patterns 120 obtained by photographing with the camera 14 are different from each other, it can be considered that the patterned light is incorrectly irradiated from the projector 12. Therefore, in this case, the measurement light irradiation position, settings, and the like of the projector 12 are adjusted so that the target irradiation position of the pattern irradiated by the projector 12 and the position of the image 152 of the patterns 120 obtained by photographing with the camera 14 are the same.

The method for correcting the intraoral scanner in accordance with the present embodiment can readily obtain image data for calibrating the camera 14 and the projector 12, respectively, without using two or more calibration plates by emitting (irradiating) the illumination light and the patterned light, respectively, onto the single first calibration plate 100 via the projector 12.

Figure 4:
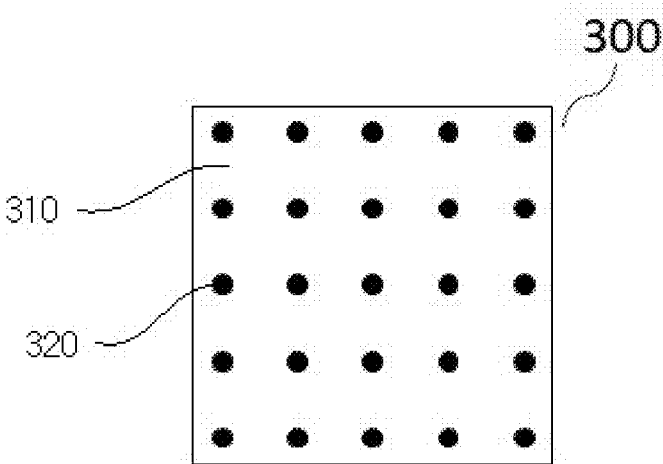
FIG. 4 is a diagram showing a second calibration plate 300 used in a method for calibrating an intraoral scanner in accordance with another embodiment of the present disclosure.

FIG. 4 is a diagram showing a second calibration plate 300 used in a method for calibrating an intraoral scanner in accordance with another embodiment of the present disclosure. The second calibration plate 300 shown in FIG. 4 is a plate having a background 310 and patterns 320 arranged at predetermined intervals within the background 310. For example, the second calibration plate 300 may be a plate of various materials, for example, a square plate of glass material, the background 310 and the patterns 320 may be formed on one side of the plate 300, and it is preferable that no additional shapes other than the patterns 320 are formed on the background 310.

The second calibration plate 300 can be formed in a variety of ways. For example, black patterns 320 may be formed and the background 310 may be formed in white by masking the background 310 excluding the pattern 320 area on a plate of white glass material and then coating with black.

The patterns 320 formed on the second calibration plate 300 are patterns arranged in a predetermined shape so that the camera 14 can be calibrated. In addition, the spacing between the patterns 320 formed on the second calibration plate 300 is set such that the pattern of the patterned light irradiated by the projector 12 is formed between the patterns 320 formed on the second calibration plate 300 (without overlapping with the patterns 320 formed on the second calibration plate 300) so as to allow the projector 12 to be calibrated. The patterns 320 formed on the second calibration plate 300 may be formed in the same way as the patterns 120 formed on the first calibration plate 100, except for the spacing between them. The dot patterns 320 formed on the second calibration plate 300 may vary depending on the size of the plate 300, but may be formed in the form of a 5×5 square matrix, as shown in FIG. 4, for example. Since the actual position and size of the patterns 320 are predetermined, an image of the patterns 320 is obtained by photographing the patterns 320 with the camera 14, and then the camera 14 may be calibrated, i.e., corrected so that the image of the patterns 320 obtained by photographing with the camera 14 corresponds to the actual position and size of the patterns 320.

Figure 5:
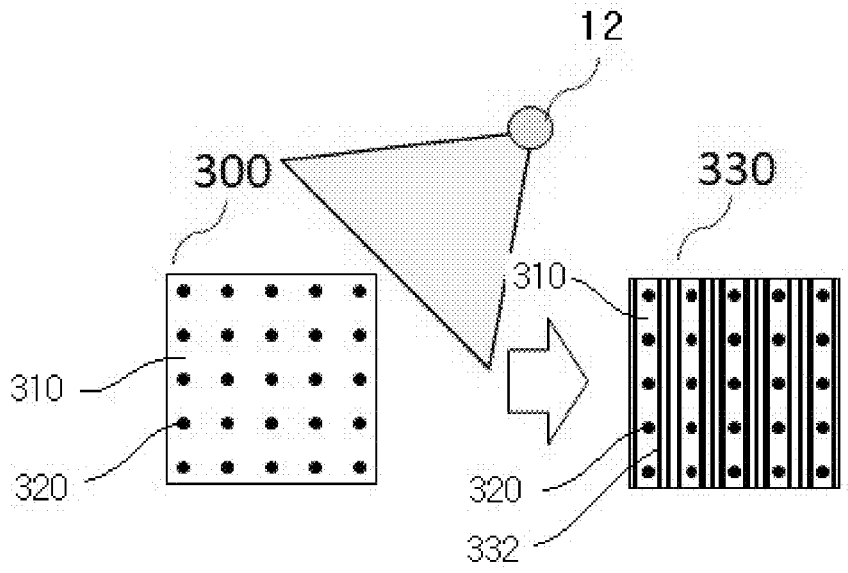
FIG. 5 is a diagram for describing a method of calibrating the camera and the projector 12 of the intraoral scanner by using the second calibration plate, according to another embodiment of the present disclosure.

FIG. 5 is a diagram for describing a method of calibrating the camera 14 and the projector 12 of the intraoral scanner by using the second calibration plate 300, according to another embodiment of the present disclosure.

In order to calibrate the camera 14 of the intraoral scanner according to the present embodiment, an image of the patterns 320 is obtained by photographing the second calibration plate 300 having the background 310 and the patterns 320 arranged at predetermined intervals within the background 310 with the camera 14.

At this time, the second calibration plate 300 may be irradiated with an illumination light by using the projector 12 as necessary. The illumination light is for obtaining an image of the patterns 320 formed on the second calibration plate 300 more easily. If an image of the patterns 320 can be obtained using the camera 14 without irradiating the illumination light, the irradiation of the illumination light is not required.

Next, the camera 14 is calibrated by comparing the image of the patterns 320 obtained by photographing with the camera 14 with the actual position of the patterns 320 formed on the calibration plate 300. Such calibration of the camera 14 can be performed in a typical manner. Specifically, the camera 14 is calibrated such that the image of the patterns 320 obtained by photographing with the camera 14 corresponds to the actual position of the patterns 320 formed on the calibration plate 100. For example, the position, settings, and the like of the camera 14 are adjusted so that the image of the patterns 320 obtained by photographing with the camera 14 and the actual position of the patterns 320 formed on the calibration plate 300 are proportional to each other without distortion.

As shown in FIG. 5, in order to calibrate the projector 12 of the intraoral scanner according to the present disclosure, the second calibration plate 300 is irradiated with a patterned light having a predetermined pattern by using the projector 12, so as to cause the pattern 332 of the patterned light to be formed in the empty space between the patterns 320 formed on the second calibration plate 300. In other words, the pattern 332 of the patterned light irradiated by the projector 12 does not overlap with the patterns 320 formed on the second calibration plate 300 but is formed between the patterns 320 formed on the second calibration plate 300. The pattern 332 of the patterned light is not particularly limited in form as long as it can be formed between the patterns 320 formed on the second calibration plate 300, and may be a pattern in the form of a stripe, as shown in FIG. 5, for example.

Next, the second calibration plate 330 with the pattern 332 of the patterned light formed thereon is photographed with the camera 14, and an image of the pattern 332 formed by the patterned light of the projector 12 is obtained.

Next, the projector 12 is calibrated by comparing the pattern image 332 of the patterned light obtained by photographing with the camera 14 with the target irradiation position of the pattern irradiated by the projector 12. Such calibration of the projector 12 can be performed in a typical manner. The calibration of the projector 12 may be performed in the same manner as in the embodiment using the first calibration plate 100 except that the pattern 332 of patterned light formed between the patterns 320 of the second calibration plate 300 is used.

The method for correcting the intraoral scanner in accordance with the present embodiment can readily obtain image data for calibrating the camera 14 and the projector 12, respectively, without using two or more calibration plates by emitting (irradiating) the patterned light onto the single second calibration plate 300 via the projector 12.

The method for calibrating an intraoral scanner in accordance with the present disclosure can improve user convenience by performing the calibration of the camera and the projector in a simplified procedure within a short time by using a single calibration plate and an illumination light and/or a patterned light of the projector.

Although the present disclosure has been described above with reference to the accompanying drawings and example embodiments, the present disclosure is not limited to what is shown in the drawings and the embodiments described above. In the following claims, reference numerals are indicated to aid understanding, but the scope of the following claims should not be limited to what is shown by the reference numerals and in the drawings and should be construed to encompass all modifications, and equivalent constructions and functions of the example embodiments.

What is claimed is:

1. A method of calibrating an intraoral scanner, comprising the steps of:

obtaining an image of patterns by photographing a calibration plate having a background and the patterns arranged at predetermined intervals within the background with a camera;

calibrating the camera by comparing the image of the patterns obtained by photographing with the camera with actual positions of the patterns formed on the calibration plate;

causing a pattern of a patterned light to be formed in an empty space between the patterns formed on the calibration plate by irradiating the calibration plate with the patterned light having a predetermined pattern by using a projector;

obtaining an image of the pattern formed by the patterned light of the projector by photographing the calibration plate with the pattern of the patterned light formed thereon with the camera; and calibrating the projector by comparing the pattern image of the patterned light obtained by photographing with the camera with a target irradiation position of a pattern irradiated by the projector, wherein the pattern of the patterned light irradiated by the projector does not overlap with the patterns formed on the calibration plate but is formed between the patterns formed on the calibration plate.

2. The method of claim 1, wherein the background and the patterns are formed on one side of the calibration plate, and no additional shapes other than the patterns are formed on the background.

* * * * *